United States Patent
Raman et al.

(10) Patent No.: US 10,098,344 B2
(45) Date of Patent: Oct. 16, 2018

(54) AGRICULTURAL ADJUVANTS AND PROCESSES FOR MAKING AND USING SAME

(71) Applicant: Celanese International Corporation, Irving, TX (US)

(72) Inventors: Narayan K. Raman, Cincinnati, OH (US); Hannah E. Toomey, Covington, KY (US); Kristin Herrel, Dallas, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 185 days.

(21) Appl. No.: 14/642,548

(22) Filed: Mar. 9, 2015

(65) Prior Publication Data

US 2016/0262375 A1    Sep. 15, 2016

(51) Int. Cl.
*A01N 25/30* (2006.01)
*A01N 25/06* (2006.01)
*A01N 57/20* (2006.01)

(52) U.S. Cl.
CPC ............. *A01N 25/30* (2013.01); *A01N 25/06* (2013.01); *A01N 57/20* (2013.01)

(58) Field of Classification Search
None
See application file for complete search history.

(56) References Cited

U.S. PATENT DOCUMENTS

| | | | |
|---|---|---|---|
| 4,104,220 A | 8/1978 | Sims | |
| 4,111,877 A | 9/1978 | Dixon et al. | |
| 4,219,454 A | 8/1980 | Iacoviello et al. | |
| 4,319,032 A | 3/1982 | Sandri et al. | |
| 4,599,417 A | 7/1986 | Sekmakas et al. | |
| 5,064,888 A | 11/1991 | Farwaha et al. | |
| 5,208,285 A | 5/1993 | Boyce et al. | |
| 5,530,056 A | 6/1996 | Farwaha et al. | |
| 6,093,856 A | 7/2000 | Cripe | |
| 6,441,082 B1* | 8/2002 | Weitzel | C04B 24/163 524/458 |
| 7,070,795 B1* | 7/2006 | Botts | A01N 25/10 424/405 |
| 8,809,234 B1 | 8/2014 | Parrish | |
| 2012/0238448 A1* | 9/2012 | Schneider | A01N 59/20 504/121 |
| 2013/0237419 A1 | 9/2013 | Shao et al. | |
| 2014/0162018 A1 | 6/2014 | Lunsford et al. | |

FOREIGN PATENT DOCUMENTS

WO     2016/015056 A1     1/2016

OTHER PUBLICATIONS

Fritz, B.K. et al. (2014). "Measuring Droplet Size of Agricultural Spray Nozzles—Measurement Distance and Airspeed Effects," *Atomization and Sprays* 24(9):747-760.
Immergut, E.H. et al. (Jan. 1, 1965). "Principles of Plasticization," Chapter 1 in *Plasticization and Plasticizer Processes*, Polytechnic Institute of Brooklyn, Brooklyn, N.Y., pp. 1-26.
O'Brien, J. (1988). "Plasticizers," in Modern Plastics Encyclopedia, McGraw Hill, New York, pp. 168-169.
Hallstar Technical Publication (Date unknown). "The Function and Selection of Ester Plasticizers," located at https://www.hallstar.com/webfoo/wp-content/uploads/The-Function-Selection-Ester-Plasticizers.pdf.
Non-Final Office Action received in U.S. Appl. No. 15/272,950, dated Dec. 14, 2017.

* cited by examiner

Primary Examiner — Johann R Richter
Assistant Examiner — Danielle Sullivan
(74) Attorney, Agent, or Firm — Kilpatrick Townsend & Stockton LLP

(57) ABSTRACT

An agricultural spray composition, comprising a vinyl ester-based polymer dispersion; a plasticizer; and an active ingredient.

16 Claims, No Drawings

AGRICULTURAL ADJUVANTS AND PROCESSES FOR MAKING AND USING SAME

FIELD OF THE INVENTION

The present invention relates generally to agricultural spray adjuvants, agricultural spray compositions, and processes for treating agricultural products using same. In particular, the present invention relates to spray adjuvants comprising an aqueous polymer dispersion and a plasticizer.

BACKGROUND OF THE INVENTION

Adjuvants are generally known as substances that are added in crop protection sprays, e.g., herbicidal formulations or agricultural spray compositions, or to spray tanks used in the dispersion of same to improve activity of an active ingredient, e.g. a herbicide, that is also present in the crop protection spray or to improve application characteristics. Spray adjuvants are generally grouped into two broad categories: special purpose adjuvants and activator adjuvants. Special purpose adjuvants are typically know to widen the range of conditions under which a given crop protection spray is useful. The special purpose adjuvant may alter the physical characteristics of the spray solution. Exemplary special purpose adjuvants include compatibility adjuvants, buffering adjuvants, antifoam adjuvants, and drift control adjuvants. Exemplary special purpose adjuvant compounds include phosphatidylcholine, alkyl polyoxyethylene ether, methylacetic (acid), soluble polymers such as xanthum gum, rheology modifiers such as polyacrylamide (EDT Concentrate) and styrene butadiene latex emulsions. Exemplary commercial products include In-Place®, InterLock®, Bond®, LI700®, and Strikeforce™. Drift control adjuvants are employed to reduce or eliminate fine spray droplet particles ("fines" or "driftable fines") that are formed when the agricultural spray composition is sprayed, e.g., from an aircraft or a ground sprayer. Driftable fines are commonly defined as droplets that are less than 150µ, e.g., less than 105µ in size (droplet diameter). By reducing or eliminating driftable fines, drift control adjuvants allow more of the deployed agricultural spray composition to reach the intended target substrate. Because driftable fines are reduced, less of the deployed agricultural spray composition drifts away and damages adjacent vegetation. Some typical drift control adjuvants include crop oil concentrates (containing 80 to 85 percent of synthetic oil, 15-20 percent of surfactants), vegetable oil concentrates (containing 50-80 percent of vegetable oils and 20 to 50 percent nonionic surfactant), oil-in-water micro emulsions, and water-in-oil invert emulsions (made) with petroleum or vegetable oils, surfactants and water.

The oil-in-water micro-emulsions and water-in-oil invert emulsions are known to be essentially solvents or emulsifiable oils and typically have lower molecular weights, e.g., from 275 g/mole to 350 g/mole. Oil-in-water micro-emulsions and water-in-oil invert emulsions often contain a petroleum or vegetable derived oil that is immiscible with water and a surfactant to emulsify the mixture to make the oil and water miscible. These emulsions, however, do suffer from several disadvantages. For example, micro-emulsion droplets may be too large to spray. Also, the micro-emulsion may become unstable and phase separate over a time. The surfactants are known to produce foam during mixing especially with certain herbicides such as glyphosates. These drawbacks make it difficult to use such emulsions with conventional spray equipment without agitation. And in the case of large size droplets, large volumes of adjuvant are required to cover the pest infested target area. With the application of large volumes of pesticides applied to foliage, damage can be caused due to the toxic effect on the foliage by overconcentration of the emulsifiers and/or oil in the large droplets applied.

Activator adjuvants are commonly used to enhance post-emergence active ingredient performance, e.g., herbicide performance. Activator adjuvants are known to increase activity, absorption into plant tissue, and rainfastness. Activator adjuvants can also decrease photodegradation of the active ingredient and also alter the physical characteristics of the spray solution. Activator adjuvants include surfactants, crop oil concentrates, nitrogen fertilizers, spreader-stickers, wetting agents, and penetrants. Although these conventional adjuvants may provide for some improvements in active ingredient and/or agricultural spray composition efficacy, the ability to reduce driftable fines is limited (often due to the high amount of surfactants that are necessarily used therewith). These high amounts of surfactants increase drift potential and increase phytotoxicity to the foliage. Some of the conventional adjuvants in particular have a limited effect on the median spray droplet size. In some cases, conventional adjuvants not only form greater amounts of driftable fines, but some of these conventional adjuvants also form greater amounts of very large droplets, e.g., greater than 730μ in size. In particular, soluble polymer based products such as polyacrylamide and xanthum gum are known to shift the entire distribution substantially to large droplet diameters and also increase relative span. The very large droplets may result in an agricultural spray composition that provides poor coverage due to rebound from the leaf surface, which in turn reduces the overall efficacy of the active ingredients. The soluble polymers also hydrate slowly and mix poorly, which leads to processing issues such as longer mixing times. And soluble polymers are also more susceptible to degrade under shear stress during application or pump transfer. Further, the required usage level for these adjuvants is often quite high, which results in unwanted phytotoxicity of the foliage due to the high surfactant concentration (as noted above).

In addition, some conventional drift reduction adjuvants have been known to have deleterious effects on the sticking and spreading of the agricultural spray composition on the intended substrate, e.g., leaf surfaces, which may result in reductions in the efficacy of the active ingredient and/or the agricultural spray composition as a whole. For example, some conventional drift reduction adjuvants can make the agricultural spray composition droplets evaporate or dry too quickly, which prevents absorption of the systemic herbicide into the leaf substrate. Also, some conventional adjuvants affect the surface tension of the agricultural spray composition such that spreading of the agricultural spray composition on the substrate, detrimentally, is limited.

Some vinyl ester-based polymer dispersions, e.g., stabilized polymer vinyl ester-based polymer dispersions, have been employed in a variety of applications including, for example, as binders for adhesives, paints and paper coating compositions. In these applications, the polymer dispersion may be used in combination with other components, e.g., plasticizers. In these cases, the polymer dispersions are present in higher concentrations, while the other components are present in lower concentrations. These concentrations are suitable for the respective application, but may not be suitable for different applications. While these polymer dispersions are known to be utilized with adhesives and paints, the use of the (vinyl ester-based) polymer dispersions in the crop protection milieu has not been contemplated.

The weight average molecular weight of these emulsions can range upwards from 250,000 g/mol to 400,000 g/mol. Importantly, these polymer dispersions differ significantly from the aforementioned oil-in-water micro-emulsions and water-in-oil invert emulsions, in both chemical composition and physical properties. For example, the oil-in-water micro-emulsions and water-in-oil invert emulsions have lower molecular weight oils and do not comprise polymers and/or the monomer precursors thereof, and, as a result, lack the defined structure of aqueous polymer dispersions. The weight average molecular weight of these emulsions can range upwards from 275 g/mol to 350 g/mol. Oil-in-water micro-emulsions and water-in-oil invert emulsions are not known to be used interchangeably with vinyl ester-based polymer dispersions.

In view of the shortcomings of conventional adjuvants, the need exists for new adjuvants that provide for improvements in overall agricultural spray composition efficacy, e.g., reductions in driftable fines and maintenance of the relative span of the droplet size.

SUMMARY OF THE INVENTION

In one embodiment, the present invention relates to an agricultural spray composition, comprising a vinyl ester-based polymer dispersion, a plasticizer, and an active ingredient (and optionally a liquid carrier, preferably water). The vinyl ester-based polymer dispersion may be stabilized, e.g., by at least one of a protective colloid and a surfactant, and preferably may comprise an aqueous dispersion of a polymer produced from one or more monomers, at least one of the monomers comprising a vinyl ester of a carboxylic acid. At least one of the monomers may comprise a vinyl ester of a carboxylic acid and having up to 20 carbon atoms. The plasticizer may be selected from the group consisting of an epoxidized methyl ester of soy oil, methyl ester of soy oil, triethylene glycol diester, polyalkylene glycols, polyether polyols, esters of canola oil, esters of castor oil, ester oils, 2,2,4-trimethyl-1,3-pentanediol monoisobutyrate, phthalates, adipic acid polyesters, trimellitates, adipates, epoxy esters, polyetheresters, epoxidized soy esters, benzoates, dipropylene glycol dibenzoate, diethylene glycol dibenzoate, and mixtures thereof (preferably being a triethylene glycol diester) and the active ingredient may be selected from the group consisting of herbicides, pesticides, fungicides, insecticides, acaricides, nematocides, foliar nutrients, defoliants, plant growth regulators, molluscidcides. Preferably, the active ingredient is selected from the group consisting of 2,4-D Dicblorophenoxyacetic acid (2,4-D), glyphosate, dicamba, triclopyr, imazapyr, sulfometuron, methyl, fluridone, clopyralid, picloram, hexazinone, chlorpyriphos, carbaryl, methomyl, ethepon, fosamine, benomyl, ferbam, zineb, and mixtures thereof. The active ingredient may be present in an amount from 0.5 to 5 wt %, based on total weight of the spray composition. The plasticizer may have a boiling point greater than 110° C. The invention may also relate to a method for producing an agricultural spray composition, comprising the steps of providing a vinyl ester-based polymer dispersion (optionally stabilized), adding to the vinyl ester-based polymer dispersion a plasticizer to form an adjuvant, and adding to the adjuvant an active ingredient to form the agricultural spray composition (and optionally adding to the adjuvant a liquid carrier). The adding may comprise adding to the vinyl ester-based polymer dispersion at least 15 wt % plasticizer. Preferably, the vinyl ester-based polymer dispersion is present in the adjuvant in an amount less than 85 wt %, based on the total weight of the adjuvant.

The vinyl ester-based polymer dispersion and the plasticizer may form an adjuvant and the adjuvant may be present in amount from 0.01 to 15 wt %, based on the total weight of the spray composition. The adjuvant may comprise greater than 15 wt % plasticizer and/or less than 85 wt % vinyl ester-based polymer dispersion. The plasticizer may be present in an amount from 15 wt % to 70 wt % based on the total weight of the adjuvant. The vinyl ester-based polymer dispersion may be a polymer produced from one or more monomers, at least one of the monomers comprising a vinyl ester of a carboxylic acid and having up to 20 carbon atoms, and may be stabilized by a protective colloid and/or a surfactant, and the one or more monomers may further comprise ethylenically unsaturated monomers capable of polymerizing with vinyl ester and ethylene. The vinyl ester preferably comprises vinyl acetate and the one or more monomers further comprise ethylene. The vinyl ester-based polymer dispersion may be protective colloid stabilized and the protective colloid is selected from the group consisting of hydroxyl ethyl cellulose, polyvinyl alcohol, polyethylene oxide, starch, and mixtures thereof (preferably hydroxyl ethyl cellulose) or the vinyl ester-based polymer dispersion may be surfactant stabilized and the surfactant is selected from the group consisting of one or more anionic and nonionic, amphoteric, and polymerizable surfactants. Preferably, the adjuvant has a pH from 3 to 8.5, and/or a static surface tension from 30 to 60 dynes/cm and/or a viscosity from 100 cp to 10000 cp. The adjuvant may be free of surfactant. The adjuvant may further comprise a viscosity modifying agent selected from the group consisting of polyvinyl alcohol, polyethylene oxides, polyethylene glycols, polypropylene glycols, cellulose derivatives, starches, attapulgites, synthetic clays, fumed silica, colloidal silica, hydrogenated castor wax, polyamide, carboxy functional acrylic, associative thickeners, alkali-swellable emulsions, alkali soluble emulsions, hydrophobically modified alkali-swellable emulsions, hydrophobically modified ethoxylated urethane resins, and mixtures thereof. The invention further contemplates a method for producing a spray adjuvant, comprising the step of providing a vinyl ester-based polymer dispersion, and adding to the vinyl ester-based polymer dispersion greater than 15 wt % of a plasticizer. Preferably, the vinyl ester-based polymer dispersion is present in an amount less than 85 wt %.

The invention further relates to a process for treating an agricultural product, comprising the steps of spraying on the agricultural product the agricultural spray composition, preferably forming droplets. Preferably, no more than 5 vol % of the droplets have a droplet size less than 105 µm and/or the droplets have an average droplet size from 50 µm to 1000 µm and/or the droplets have an average droplet size from 200 µm to 300 µm, and/or the droplets have an evaporation rate from 1% weight loss/min to 8% weight loss/min, and/or the rate of decrease in dynamic surface tension of the droplets is less than 10 mN/m-min, and/or the droplets have an average contact angle from 35° to 75°, and/or the spread diameter of the droplets ranges from 4.0 to 7.0 mm. The agricultural spray composition, when sprayed, may yield droplets having less than 7 wt % droplets less than 105µ in size, a relative span less than 1.2, and a Dv50 greater than 250µ.

DETAILED DESCRIPTION OF THE INVENTION

It has now been discovered that the combination of a vinyl ester-based polymer dispersion, a plasticizer, and an agriculturally active ingredient provides for an agricultural spray composition having improved properties. In some embodiments, the polymer dispersion and the plasticizer combine to form an adjuvant.

In some embodiments, the agricultural spray composition, advantageously demonstrates, inter alia, a synergistic reduction in driftable fines and/or maintenance of the relative span of droplet size as compared to agricultural spray compositions employing conventional agricultural spray adjuvants or no adjuvants at all. The vinyl ester-based polymer dispersion may be any suitable one, e.g., a stabilized polymer dispersion that may be stabilized with a protective colloid and/or a surfactant. In some embodiments, the polymer dispersion may be produced from one or more monomers, at least one of the monomers comprising a vinyl ester of a carboxylic acid and having up to 20 carbon atoms, e.g., up to 15 carbon atoms or up to 10 carbon atoms, stabilized by a protective colloid or a surfactant. Preferably the vinyl ester of a carboxylic acid comprises vinyl acetate. In one embodiment, the one or more monomers further comprise ethylene. The plasticizer preferably comprises a triethylene glycol diester, e.g., triethylene glycol di-2-ethylhexanoate ("3G8"). In some embodiments, the plasticizer has a high boiling point, e.g., greater than 110° C., greater than 150° C., or greater than 250° C. and/or a low volatility. The combination of the adjuvant (the polymer dispersion and the plasticizer) with the active ingredient provides for the improved agricultural spray composition.

Conventional compositions may comprise such a polymer dispersion and a plasticizer. These conventional compositions, however, are utilized in adhesive- and paint-related applications and are not known to be utilized in combination with an active ingredient to form an agricultural spray composition. Thus, these conventional compositions (and teachings relating thereto) are not relevant to the present adjuvant and agricultural spray composition. Importantly, in conventional applications, the polymer dispersions are present in higher concentrations, while the other components, e.g., the plasticizers, are present in lower concentrations. For example, in a conventional application, a polymer dispersion/plasticizer composition may comprise greater than 85 wt % polymer dispersion and less than 15 wt % plasticizer.

The present invention, however, utilizes the polymer dispersion and the plasticizer for entirely different applications and in entirely different proportions (in the adjuvant or the agricultural spray composition). In one embodiment, the plasticizer is present in an amount from 15 wt % to 70 wt %, e.g., from 15 wt % to 60 wt %, from 20 wt % to 50 wt %, or from 20 wt % to 40 wt %. In terms of limits, the plasticizer may be present in an amount less than 70 wt %, e.g., less than 60 wt %, less than 50, wt %, or less than 40 wt %. The plasticizer may be present in an amount greater than 15 wt/%, e.g., greater than 20 wt %, greater than 25, wt %, or greater than 30 wt %, in some embodiments, the polymer dispersion is present in an amount from 30 wt % to 85 wt %, e.g., from 35 wt % to 80 wt %, from 35 wt % to 75 wt %, or from 40 wt % to 70 wt %. In terms of limits, the polymer dispersion may be present in an amount less than 85 wt %, e.g., less than 80 wt %, less than 75 wt %, or less than 70 wt %. The polymer dispersion may be present in an amount greater than 35 wt %, e.g., greater than 40 wt %, greater than 45, wt %, or greater than 50 wt %. Weight percentage ranges and limits are based on the total weight of the adjuvant. The polymer dispersion is present in concentrations much lower than in typical applications, e.g., adhesives, and the plasticizer is present in amounts much lower than in typical applications.

In one embodiment, the concentration of plasticizer is more than 25% of the concentration of the polymer dispersion, e.g., more than 30%, more than 40%, more than 50%, more than 60%, more than 70%, more than 80%, or more than 90%, based on the concentration of the polymer dispersion. In one embodiment, there is more plasticizer than polymer dispersion in the adjuvant.

In one embodiment, the adjuvant has a static surface tension from 30 dynes/cm to 60 dynes/cm, e.g., 35 dynes/cm to 55 dynes/cm or 40 dynes/em to 50 dynes/cm. In some embodiments the adjuvant has a viscosity from 100 cp to 10000 cp, e.g., from 200 cp to 6000 cp for from 500 cp to 4000 cp. In some embodiments, the pH of the adjuvant and/or an adjuvant concentrate may be between 3.0 to 8.5, e.g., from 3.5 to 7, or from 4 to 6.

The invention also relates to a method for producing a spray adjuvant. The method comprises the steps of providing the vinyl ester-based polymer dispersion and adding a plasticizer to the vinyl ester-based polymer dispersion. Preferably, the greater than 15 wt % of plasticizer, is added to the polymer dispersion.

Plasticizer

The combination of plasticizer and polymer dispersion surprisingly yields an adjuvant composition having synergistic properties and characteristics. In some cases, the use of specific concentrations of plasticizer and polymer dispersion contributes to the synergistic properties and characteristics. It is believed that the synergy comes from the combination being able to reduce driftable fines using both mechanisms. In some embodiments, without being bound by theory, it is believed that most of the plasticizer (in the adjuvant) is able to preferentially enter into the polymer colloid of the aqueous polymer dispersion with the rest likely present in the water phase as emulsified droplets. The plasticizer in the polymer phase is believed to interpose between the individual strands of polymers thereby causing breakdown of polymer-polymer interactions. This beneficially makes the polymer more porous and flexible, and makes its structure less cohesive. Plasticizers having polarity that is similar to the polymer but different from water may also soften and swell the polymer colloid (latex colloids), which aids in overcoming resistance to deformation. As a result, the plasticized aqueous polymer dispersion deforms at a lower tensile force as compared to without plasticizer. This effect in turn enhances the film elongation effect. The plasticizers are also known to decrease the surface tension at the polymer surface. In effect, it is postulated that the polymer phase acts as a carrier for the plasticizer. The resulting adjuvant is essentially a single phase and may be easily mixed in an agricultural spray composition with minimal mixing, unlike conventional oil based adjuvants, which are typically immiscible with water. The single phase nature of the inventive adjuvant composition allows it to be used in crop protection sprays with minimal or no use of surfactants. In addition to the ability to alter the physical and mechanical properties of the polymers of the aqueous polymer dispersion, the plasticizers may be able to diffuse out of the polymer to beneficially aid in adhesion and spreading on the leaf surface.

Further, because of the high boiling points of the plasticizers and because the fact that most of the plasticizer is occluded in the polymer colloid and not readily exposed to environment, the plasticizers can advantageously keep the sprayed droplets wet for a longer period of time, which allows more time for the active ingredient(s) to diffuse through the leaf cuticle and be absorbed by the plant.

In some cases, efficient plasticizers generally meet a basic requirement, namely, that all the intermolecular forces involved (between plasticizer and plasticizer, between polymer and polymer, between plasticizer and polymer) are of the same order of magnitude. The thermodynamic basis for such interactions is expressed by Hildebrand solubility parameters, defined as the square root of cohesive energy density. Plasticizer compatibility with an amorphous polymer such as the polymer dispersions used in this invention, S, normally requires values that do not differ by more than ±1.5 (cal./cc). Solubility parameters for both polymers and plasticizers are conveniently calculated by the additive method of Small, who has derived individual parameters for various atoms and groups in the molecules. Compilations of molar attraction constants, commonly known as Small's constants, are given in many references, e.g., "The Function and Selection of Ester Plasticizers," Halistar Technical Publication, O'Brien, J. L., "Plasticizers", in Modern Plastics Encyclopedia, McGraw Hill, New York, 1988, p. 168, Polymer/Plasticizer Polarity Chart (brochure), The C. P. Hall Company, 311 S. Wacker, Chicago, Ill. 60606)

In addition to the balance of intermolecular forces, efficient plasticizers show low volatility, high solvent power, compatibility with polymer, similar polarity to the polymer, and temperature stability. These properties control the how fast the plasticizer can diffuse in and out of the polymer and it ability to interpose between the polymer chains. The choice of a plasticizer, therefore, usually involves a compromise since the requirements for good solvent power, compatibility, efficiency, and permanence, cannot all be met simultaneously all the time, (Principles of Plasticization, Edmund H. Immergut and Herman F. Mark, *Polytechnic Institute of Brooklyn*, Brooklyn, N.Y., Chapter 1, http://pubs.acs.org. In one embodiment, the plasticizer is a particular plasticizer selected from the group consisting of a triethylene glycol diester, e.g., triethylene glycol di-2-ethylhexoate ("3G8"), polyalkylene glycols, polyether polyols, esters of canola oil, esters of castor oil, 2,2,4-trimethyl-1,3-pentanediol monoisobutyrate, phthalates, non-phthalates (adipic acid polyesters, trimellitates, adipates, epoxy esters, polyetheresters, benzoates, dipropylene glycol dibenzoate, diethylene glycol dibenzoate), epoxidized methyl ester of soy oil, methyl ester of soy oil, and mixtures thereof. The plasticizer preferably comprises a triethylene glycol diester, e.g., triethylene glycol di-2-ethylhexoate ("3G8"). In one embodiment, the plasticizer does not include propylene glycol and/or glycol ethers. Generally speaking, these plasticizers have a unique combination of properties that leads to the surprising adjuvant compositions discussed herein, e.g., the plasticizers are hydrophobic, immiscible with water, have high boiling points, and/or show good plasticizer response. In an embodiment, the plasticizer response ranges from 0.5 to 15, e.g., from 1.2 to 8.

Plasticizer response may be measured as follows: measuring the initial viscosity of 200 grams of the polymer dispersion, e.g., using a Brookfield Viscometer, RV, Spindle #5, 20 rpm; stirring the polymer dispersion, e.g., at 500 rpm, and adding 50 grams of plasticizer, e.g., over 10 minutes (stirring speed may be increased to insure good mixing; the blend may be further stirred, e.g., for 15 minutes, once all the plasticizer is added); remeasuring the viscosity of the blend, e.g., at 1 hour and then at 24 hours; and calculating the plasticizer response as the ratio of final viscosity of the blend at 24 hours to the original viscosity of the neat polymer without the plasticizer.

Suitable commercial plasticizers include, but are not limited to, Celvaset™ PL-1000, Soygold® 2500, Optifilm™ Enhancer 400, Steposol® SBD; Loxanol® EFC 300, Lusolvan® FBH, Pluriol® WS 600, ADM CA 118, Pluracoat™ CA 100, Pluracoat™ CA 110, Pluracoat™ CA 120, OxiCure® 2000, Soyanol SGE 40, Texanol™, and Benzoflex™ 50.

The adjuvant may further comprise a viscosity modifying agent. In some embodiments, the viscosity modifying agent is selected from the group consisting of polyvinyl alcohol, polyethylene oxides, polyethylene glycols, polypropylene glycols, cellulose derivatives, starches, attapulgites, synthetic clays, fumed silica, colloidal silica, hydrogenated castor wax, polyamide, carboxy functional acrylic, associative thickeners, alkali-swellable emulsions, alkali soluble emulsions, hydrophobically modified alkali-swellable emulsions, hydrophobically modified ethoxylated urethane resins, and mixtures thereof Polymer Dispersion The polymer dispersion may vary widely and will be produced from one or more monomers. The monomer(s) preferably comprise a vinyl ester of a carboxylic acid and having up to 20 carbon atoms, e.g., up to 15 carbon atoms or up to 10 carbon atoms.

The aqueous polymerization mixture can be substantially free of seed polymer particles, by which is meant that that the mixture contains less than 5 wt %, preferably less than 1 wt % and most preferably no added seed polymer particles.

Monomers

The (aqueous) polymerization mixture used to produce the present polymer dispersion comprises one or more free-radically polymerizable main monomers. Suitable main monomers are selected from $C_1$-$C_{20}$-alkyl (meth)acrylates, vinyl esters of carboxylic acids with up to 20 carbons, vinyl-aromatic compounds having up to 20 carbons, ethylenically unsaturated nitriles, vinyl halides, vinyl ethers of $C_1$-$C_{10}$ alcohols, $C_2$-$C_8$ aliphatic hydrocarbons with 1 or 2 double bonds, and mixtures of these monomers. In one embodiment, the polymer dispersion comprises monomers comprising a vinyl ester of a carboxylic acid.

Preferred alkyl (meth)acrylates are $C_1$-$C_{10}$-alkyl (meth) acrylates, such as methyl methacrylate, methyl acrylate, n-butyl acrylate, ethyl acrylate and 2-ethylhexyl acrylate. Mixtures of alkyl (meth)acrylates can also be employed.

Examples of suitable vinyl esters of $C_1$-$C_{20}$ carboxylic acids include vinyl acetate, vinyl propionate, vinyl laurate, vinyl stearate, vinyl benzoate, vinyl 2-ethyl hexanoate and Versatic acid vinyl esters. Preferably the vinyl ester of a carboxylic acid comprises vinyl acetate.

Suitable vinyl-aromatic compounds include vinyltoluene, α- and p-methylstyrene, α-butylstyrene, 4-n-butylstyrene, 4-n-decyl-styrene and, preferably, styrene.

Examples of suitable nitriles include acrylonitrile and methacrylonitrile.

Suitable vinyl halides include chloro-, fluoro- or bromo-substituted ethylenically unsaturated compounds, such as vinyl chloride and vinylidene chloride.

Examples of vinyl ethers are vinyl methyl ether and vinyl iso-butyl ether, with preference being given to vinyl ethers of $C_1$-$C_4$ alcohols.

Examples of suitable $C_2$-$C_8$ aliphatic hydrocarbons with one olefinic double bond include ethene and propene, whereas representative examples of $C_2$-$C_8$ aliphatic hydrocarbons having two olefinic double bonds include butadiene, isoprene and chloroprene.

In one embodiment, the present polymer dispersion is produced from a mixture of free-radically polymerizable main monomers comprising from 50 wt % to 99 wt % vinyl acetate and from 1 wt % to 40 wt % ethylene.

Co-Monomers

In addition to the main monomers discussed above, the aqueous polymerization mixture used to produce the present polymer dispersion may comprise up to 10 wt % of auxiliary co-monomer(s) based on the total weight of monomers in the mixture. Such auxiliary co-monomers can be those which promote better film or coating performance by the compositions herein or can provide films and coatings of desirable properties. Such desirable properties can include, for example, enhanced adhesion to low surface energy surfaces or substrates, less rebound on impacting a surface, improved spreading on waxy surfaces, longer open time, and improved resistance to film or coating drying and cracking. The optional co-monomers useful for incorporation into the emulsion copolymers of the compositions herein are those which contain at least one polymerizable double bond along with one or more additional functional moieties. Preferably, the co-monomers comprise ethylenically unsaturated monomers capable of polymerizing with the vinyl ester. Suitable auxiliary co-monomers include unsaturated organic acids, unsaturated silanes, glycidyl co-monomers, ureido co-monomers, co-monomers with crosslinkable functions, crosslinking co-monomers and combinations thereof.

Suitable auxiliary co-monomers including unsaturated organic acids comprise ethylenically unsaturated carboxylic acids and anhydrides and amides thereof, ethylenically unsaturated sulfonic acids, and ethylenically unsaturated phosphonic acids.

For example, the auxiliary monomer may comprise an ethylenically unsaturated $C_3$-$C_8$ monocarboxylic acid and/or an ethylenically unsaturated $C_4$-$C_8$ dicarboxylic acid, together with the anhydrides or amides thereof. Examples of suitable ethylenically unsaturated $C_3$-$C_8$ monocarboxylic acids include acrylic acid, methacrylic acid and crotonic acid. Examples of suitable ethylenically unsaturated $C_4$-$C_8$ dicarboxylic acids include maleic acid, fumaric acid, itaconic acid and citraconic acid.

Examples of suitable ethylenically unsaturated sulfonic acids include those having 2-8 carbon atoms, such as vinylsulfonic acid, 2-acrylamido-2-methylpropanesulfonic acid, 2-acryloyloxyethanesulfonic acid and 2-methacryloyloxyethanesulfonic acid, 2-acryloyloxy- and 3-methacryloyloxypropanesulfonic acid. Examples of suitable ethylenically unsaturated phosphonic acids also include those having 2-8 carbon atoms, such as vinylphosphonic acid and ethylenically unsaturated polyethoxyalkyletherphosphates.

In addition to or instead of said acids, it is also possible to use the salts thereof, preferably the alkali metal or ammonium salts thereof, particularly preferably the sodium salts thereof, such as, for example, the sodium salts of vinylsulfonic acid and of 2-acrylamidopropanesulfonic acid.

Unsaturated silanes useful as auxiliary co-monomers can generally correspond to the structural Formula I:

Formula I

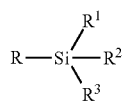

in which R denotes an organic radical olefinically unsaturated in the ω-position and $R^1$ $R^2$ and $R^3$ which may be identical or different, denote the group —OZ, Z denoting hydrogen or primary or secondary alkyl or acyl radicals optionally substituted by alkoxy groups. Suitable unsaturated silane compounds of the Formula I are preferably those in which the radical R in the formula represents an ω-unsaturated alkenyl of 2 to 10 carbon atoms, particularly of 2 to 4 carbon atoms, or an ω-unsaturated carboxylic acid ester formed from unsaturated carboxylic acids of up to 4 carbon atoms and alcohols carrying the Si group of up to 6 carbon atoms. Suitable radicals $R^1$, $R^2$, $R^3$ are preferably the group —OZ, Z representing primary and/or secondary alkyl radicals of up to 10 carbon atoms, preferably up to 4 carbon atoms, or alkyl radicals substituted by alkoxy groups, preferably of up to 3 carbon atoms, or acyl radicals of up to 6 carbon atoms, preferably of up to 3 carbon atoms, or hydrogen. Most preferred unsaturated silane co-monomers are vinyl trialkoxy silanes.

Examples of preferred silane compounds of the Formula I include γ-methacryloxypropyltris(2-methoxyethoxy)silane, vinylmethoxysilane, vinyltriethoxysilane, vinyldiethoxysilanol, vinylethoxysilanediol, allyltriethoxysilane, vinyltripropoxysilane, vinyltriisopropoxysilane, vinyltributoxysilane, vinyltriacetoxysilane, trimethylglycolvinylsilane, γ-methacryloxypropyltrimethylglycolsilane, γ-acryloxypropyltriethoxysilane and γ-methacryloxypropyltrimethoxysilane.

Glycidyl compounds can also be used as optional auxiliary co-monomers to impart epoxy-functionality to the emulsion copolymer. Examples of suitable glycidyl optional co-monomers include glycidyl acrylate, glycidyl methacrylate, allyl glycidyl ether, and vinyl glycidyl ether.

Another type of optional co-monomer comprises cyclic ureido co-monomers. Cyclic ureido co-monomers are known to impart improved wet adhesion properties to films and coatings formed from copolymers containing these co-monomers. Cyclic ureido compounds and their use as wet adhesion promoting co-monomers are disclosed in U.S. Pat. Nos. 4,104,220; 4,111,877; 4,219,454; 4,319,032; 4,599,417 and 5,208,285. The disclosures of all of these U.S. patents are incorporated herein by reference in their entirety.

Another type of optional co-monomer comprises co-monomers with crosslinkable functions such as N-methylolacrylamide, N-methylolmethacrylamide, N-methylolallylcarbamate, N-methylolmaleimide, N-methylolmaleamic acid, and the N-methylol amides of aromatic vinyl carboxylic acids, such as N-methylol-p-vinylbenzamide. N-ethanol (meth)acrylamide, N-propanol(meth)acrylamide, the N-methylol esters or N-alkyl ethers or Mannich bases of N-methylol(meth)acrylamide or N-methylolallylcarbamate, acrylamidoglycolic acid and/or its salts, methyl acrylamidomethoxyacetate or N-(2,2-dimethoxy-1-hydroxyethyl) acrylamide.

A further group of comonomers suitable for preparing the emulsion polymers used herein comprises crosslinking monomers, such as comonomers with polyethylene unsaturation, and hence with a crosslinking action. Examples include diallyl phthalate, diallyl maleate, triallyl cyanurate, tetraallyloxyethane, divinylbenzene, butane-1,4-diol dimethacrylate, triethylene glycol dimethacrylate, divinyl adipate, allyl (meth)acrylate, vinyl crotonate, methylenebisacrylamide, hexanediol diacrylate, pentaerythritol diacrylate and trimethylolpropane triacrylate.

Stabilizers

The polymer dispersion, in some embodiments, may be a stabilized polymer dispersion. The stabilized polymer dispersion may be stabilized by a suitable stabilizer, e.g., a protective colloid, a surfactant, or a mixture thereof. Generally, the stabilizer composition comprises one or more stabilizers selected from protective colloids, anionic and/or non-ionic surfactants and mixtures thereof. Generally, the stabilizer(s) are present in the aqueous polymerization mixture in an amount between 0.5 wt % and 15 wt %, e.g., between 1 wt % and 12 wt % or between 2 wt % and 10 wt %, by weight based on the total weight of monomer(s) in the polymer dispersion. In terms of upper limits, the stabilizer may be present in an amount less than 15 wt %, e.g., less than 12 wt % or less than 10 wt %. In terms of lower limits, the stabilizer may be present in an amount greater than 0.5 wt %, e.g., greater than 1 wt % or greater than 2 wt %.

In one embodiment, the polymer dispersion is stabilized by a protective colloid, and the protective colloid may vary widely. Suitable protective colloids for use as one or more of the further stabilizer(s) include polyvinyl alcohols, polyvinyl pyrrolidone, methylcelluloses, hydroxyethyl- and propylcelluloses, and also sodium carboxymethylcellulose, gelatin, casein, starch, gum arabic, hydroxy ethyl starch and sodium alginate. Suitable polyvinyl alcohols for use as a further stabilizer are substantially free of acid groups and have a molar degree of hydrolysis of at least 86. These standard grade polyvinyl alcohols have Höppler viscosities which are chosen to match the desired end viscosity of the dispersion. Conveniently these standard grades comprise a mixture of at least two polyvinyl alcohols to adjust the viscosity of the polymer dispersion. In one embodiment, the at least one further stabilizer comprises a polyvinyl alcohol having a lower Höppler viscosity value for example in a 4 weight % aqueous solution at 20° C. of 4.8 to 5.8 mPa·s and a further polyvinyl alcohol having a higher Höppler viscosity value for example in a 4 weight % aqueous solution at 20° C. of 27 to 33 mPa·s.

In some embodiments, the protective colloid is selected from the group consisting of hydroxyl ethyl cellulose, polyvinyl alcohol, polyethylene oxide, starch, and mixtures thereof. Generally speaking, a protective colloid is a compound or composition that stabilizes the polymer. In some cases the protective colloid is disposed on the surface of the polymer(s) and coats the polymer(s), which results in stabilization. Preferably, the protective colloid comprises hydroxyl ethyl cellulose.

In some cases where the polymer dispersion is stabilized by a protective colloid, the dispersion and/or the adjuvant as a whole, may contain little if any surfactant emulsifier, e.g., the dispersion and or the adjuvant is substantially surfactant free, e.g., less than 0.1 wt %, less than 0.05 wt %, less than 0.03 wt %, or less than 0.01 wt % surfactant. Without being bound by theory, it is believed that the low surfactant content beneficially results in the reduction of driftable fines. A water molecule within the bulk of water experiences attractions to neighboring water molecules in all directions. But since these attractions average out to zero, there is no net force on the water molecule. However, the water molecules at the surface of a quantity of water are subject to unequal forces. Typically, a smaller surface area usually lowers the overall potential energy thereof. Thus intermolecular attractive forces act to minimize the surface area of a liquid. The geometric shape that has the smallest ratio of surface area to volume is the sphere, so very small quantities of liquids tend to form spherical drops. There is a change in pressure across a curved surface or interface such as a sphere. The pressure change is represented by Young-Laplace equation, as shown in Formula I below, where $\Delta P$ is the Laplace pressure, R is the radius of curvature of the surface, $\eta$ is the surface tension. A smaller droplet size (smaller radius) has greater internal pressure. Hence the pressure in a smaller bubble would be much higher in comparison to the pressure inside a larger bubble, which would make the bubbles inherently unstable, e.g., the bubbles would burst. It is postulated that surfactants reduce the surface tension of water, e.g., by a factor of 3 or more, thus reducing the internal pressure and making the smaller water droplets more stable. Accordingly, it is believed that highly surfactant-loaded crop protection sprays can generate significant amount of driftable fines by stabilizing these small droplets.

$$\Delta P = P_{inside} - P_{outside} = (4\eta)/R \qquad \text{Formula I}$$

In some cases, the dispersion and/or the adjuvant as a whole, may contain little if any protective colloid stabilizer, e.g., the dispersion and or the adjuvant is substantially protective colloid free, e.g., the stabilizing system comprises less than 1.0 pphm of protective colloid, less than 0.5 pphm protective colloid, or less than 0.1 pphm protective colloid, (see US patent 20140162018, section 0013

In some embodiments, the polymer dispersion is stabilized with a surfactant emulsifier, and the surfactant emulsifier may vary widely. In some embodiments, the surfactant emulsifier is selected from the group consisting of one or more anionic and nonionic surfactant emulsifiers. Amphoteric and/or polymerizable surfactants may also be employed, alone or in combination with the anionic and/or nonionic surfactants.

The nonionic surfactant emulsifiers may vary widely. Some exemplary nonionic surfactant emulsifiers include, but are not limited to, polyoxyethylene condensates, e.g., polyoxyethylene aliphatic ethers, such as polyoxyethylene lauryl ether and polyoxyethylene oleyl ether; polyoxyethylene alkaryl ethers, such as polyoxyethylene nonylphenol ether and polyoxyethylene octylphenol ether; polyoxyethylene esters of higher fatty acids, such as polyoxyethylene laurate and polyoxyethylene oleate; condensates of ethylene oxide with resin acids and tall oil acids; polyoxyethylene amide; amine condensates such as N-polyoxyethylene lauramide, and N-lauryl-N-polyoxyethylene amine; and polyoxyethylene thio-ethers such as polyoxyethylene n-dodecyl thio-ether. In a preferred embodiment, the surfactant is sodium dioctyl sulfosuccinate, e.g., Aerosol® OT-75 PG.

Other suitable nonionic surfactant emulsifiers include, but are not limited to, a series of surface active agents available from BASF under the Pluronic® and Tetronic® trade names. Some Pluronic surfactants are ethylene oxide (EO)/Propylene oxide (PO)/ethylene oxide block copolymers that are prepared by the controlled addition of PO to the two hydroxyl groups of propylene glycol. EO is then added to sandwich the hydrophobe between two hydrophilic groups. The preparation methods may be controlled such that the length constitutes from 10% to 80% (w/w) of the final molecule. Other Pluronic surfactants are PO/EO/PO block copolymers prepared by adding EO to ethylene glycol to provide a hydrophile of designated molecular weight. PO is then added to obtain hydrophobic blocks on the outside of the molecule. Exemplary Tetronic surfactants are tetrafunctional block copolymers derived from the sequential addition of PO and EO to ethylene-diamine. Other Tetronic surfactants may be produced by the sequential addition of EO and PO to ethylene-diamine.

Other suitable nonionic surfactants include, but are not limited to, a series of ethylene oxide adducts of acetyleneic glycols, sold commercially by Air Products under the Surfynol™ trade name.

Additional suitable nonionic surfactants include acyl, alkyl, oleyl and alkylaryl ethoxylates. Examples include ethoxylated mono-, di- and trialkylphenols (EO: from 3 to 50, alkyl substituted radical: $C_4$ to $C_{12}$) and ethoxylated fatty alcohols (EO: from 3 to 80; alkyl radical: $C_8$ to $C_{36}$), especially $C_{12}$-$C_{14}$-fatty alcohol ethoxylates, $C_{13}$-$C_{15}$-oxo alcohol ethoxylates, $C_{16}$-$C_{18}$-fatty alcohol ethoxylates, $C_{1-10}$-oxo alcohol ethoxylates, $C_{1-3}$-oxo alcohol ethoxylates, polyoxyethylene sorbitanmonooleate with ethylene oxide groups, copolymers of ethylene oxide and propylene oxide with a minimum content of 10% by weight of ethylene oxide, the polyethylene oxide ethers of oleyl alcohol and the polyethylene oxide ethers of nonylphenol. Particularly suitable are the polyethylene oxide ethers of fatty alcohols, especially those of $C_{12}$-$C_{14}$-fatty alcohols.

Exemplary anionic surfactants include, but are not limited to, alkyl aryl sulfonates, alkali metal alkyl sulfates, sulfonated alkyl esters and fatty acid soaps-specific examples include sodium dodecylbenzene sulfonate, sodium butylnaphthalene sulfonate, sodium lauryl sulfate, disodium dodecyl diphenyl ether disulfonate, N-octadecyl sulfosuccinate and dioctyl sodiumsulfosuccinate.

Additional suitable anionic surfactant emulsifiers include sodium, potassium and ammonium salts of straight-chain aliphatic carboxylic acids of chain length $C_{12}$-$C_{20}$, sodium hydroxyoctadecanesulfonate, sodium, potassium and ammonium salts of hydroxy fatty acids of chain length $C_{12}$-$C_{20}$ and their sulfation and/or acetylation products thereof, alkyl sulfates, also in the form of triethanolamine salts, alkyl-($C_{10}$-$C_{20}$)-sulfonates, alkyl($C_{10}$-$C_{20}$)-arylsulfonates, dimethyldialkyl-($C_8$-$C_{18}$)-ammonium chloride, and sulfation products thereof, alkali metal salts of sulfosuccinic esters with aliphatic saturated monohydric alcohols of chain length $C_4$-$C_{16}$, sulfosuccinic 4-esters with polyethylene glycol ethers of monohydric aliphatic alcohols of chain length $C_{10}$-$C_{12}$ (disodium salt), sulfosuccinic 4-esters with polyethylene glycol nonylphenyl ether (disodium salt), sulfosuccinic acid biscyclohexyl ester (sodium salt), lignosulfonic acid and the calcium, magnesium, sodium and ammonium salts thereof, resin acids, hydrogenated and dehydrogenated resin acids and alkali metal salts thereof, sodium (dodecylated diphenyl ether) disulfonate and sodium laurylsulfate, or ethoxylated sodium lauryl ether sulfate. It is also possible to use mixtures of ionic surfactant emulsifiers. Additional amphoterica and/or polymerizable surfactants are disclosed in U.S. Pat. Nos. 5,064,888 and 5,530,056)

Polymerization Process

The desired polymer dispersion may be produced by free radical emulsion polymerization of the aqueous polymerization mixture described herein in the presence of one or more free radical initiators.

A preferred free radical initiator which is used in the beginning of the polymerization is a redox initiator system comprising an oxidizing agent having a water solubility less than or equal to 15 weight %, since these are found to produce polymer dispersions with less agglomeration of the polymer particles and hence lower viscosity of the final polymer dispersion, as well as particles of more spherical shape. Examples of such oxidizing agents include organic peroxides, such as benzoyl peroxide, lauryl peroxide, t-butyl peroxide, azoisobutyronitrile and t-butyl hydroperoxide. The preferred oxidizing agent is t-butyl hydroperoxide. Alkali metal salts of oxymethanesulfinic acid, hydroxylamine salts, sodium dialkyldithiocarbamate, sodium bisulfite, ammonium bisulfite, sodium dithionite, diisopropyl xanthogen disulfide, ascorbic acid, tartaric acid, and isoascorbic acid can be used as reducing agents.

Typically, each of the oxidizing agent and the reducing agent is charged to the reaction mixture prior to polymerization in an amount from about 0.01% to about 1.0%, preferably from about 0.02% to about 0.5%, more preferably from about 0.025% to about 0.2%, by weight based on total weight of co-monomers. Generally, the molar ratio of oxidizing agent to reducing agent in the redox initiator system is from 10:1 to 1:10.

The redox initiator system used herein can also optionally comprise catalyzing metal salts of iron, copper, manganese, silver, platinum, vanadium, nickel, chromium, palladium, or cobalt. These catalyzing salts may be used at levels of from about 0.1 to about 100 ppm, with or without metal complexing agents. Preferably iron or cobalt are used.

The polymerization may be carried out in one, two or more stages using any known polymerization reactor system, such as a batch, loop, continuous, or cascade reactor system.

The polymerization temperature generally ranges from about 20° C. to about 150° C., more preferably from about 50° C. to about 120° C. The polymerization generally takes place under either atmospheric or high pressure if appropriate, preferably from about 2 to about 150 bar, more preferably from about 5 to about 100 bar. Polymers used in this invention may also be made efficiently in low pressure polymerizations of vinyl acetate polymers, e.g., pressures lower than 250 psi. The reaction is desirably performed at pressures less than 100 psi, less than 50 psi, and more preferably at substantially atmospheric pressure, that is 14.7 psi+/−10 psi.

In a typical polymerization procedure involving, for example, vinyl acetate copolymer dispersions, the vinyl acetate, stabilizing system and any other co-monomers can be polymerized in an aqueous medium under pressures up to about 120 bar in the presence the specified stabilizers and initiators. Atmospheric pressure polymerization is preferable for both batch and continuous reactors. The aqueous reaction mixture in the polymerization vessel can be maintained by a suitable buffering agent at a pH of about 2 to about 7.

The manner of combining the several polymerization ingredients, i.e., stabilizing system, co-monomers, initiator system components, etc., can vary widely. Generally an aqueous medium containing at least part of the stabilizing system can be initially formed in a polymerization vessel with the various other polymerization ingredients being added to the vessel thereafter.

Co-monomers can be added to the polymerization vessel continuously, incrementally or as a single charge addition of the entire amounts of co-monomers to be used. Co-monomers can be employed as pure monomers or can be used in the form of a pre-mixed emulsion. When present, ethylene as a co-monomer can be pumped into the polymerization vessel and maintained under appropriate pressure therein.

It is possible for the total amount of redox initiator system to be included in the initial charge to the reactor at the beginning of the polymerization. Preferably, however, a portion of the initiator is included in the initial charge at the beginning, and the remainder is added after the polymerization has been initiated, in one or more steps or continuously. In a preferred embodiment a first redox initiator system is used in the initial charge at the beginning of the polymerization comprising an oxidizing agent having a water solubility less than or equal to 15 weight %, The reaction is then continued by a second initiator system which can be the same or different from the first redox initiator system. The second initiator system can be a redox initiator system or a thermal initiator system. In a preferred embodiment the reaction is continued by means of a different initiator system which can be a thermal initiator system comprising an oxidizing agent having a water solubility of greater than 15 weight %. Examples for such oxidizing agents are hydrogen peroxide, ammonium-sodium- or potassium persulfates, peroxidisulfates or water soluble azoamidines.

As mentioned previously, the present polymerization process is normally conducted without the use of a seed latex.

On completion of the polymerization, a further, preferably chemical after treatment, especially with redox catalysts, for example combinations of the abovementioned oxidizing agents and reducing agents, may follow to reduce the level of residual unreacted monomer on the product. In addition, residual monomer can be removed in known manner, for example by physical demonomerization, i.e. distillative removal, especially by means of steam distillation, or by stripping with an inert gas. A particularly efficient combination is one of physical and chemical methods, which permits lowering of the residual monomers to very low contents (<1000 ppm, preferably <100 ppm).

Agricultural Spray Composition

As noted above, in addition to the inventive adjuvant, the present invention relates to an agricultural spray composition. The agricultural spray composition comprises the agricultural spray adjuvant discussed herein, as well as an active ingredient (and optionally a liquid carrier). The agricultural spray composition may further comprise optional components such as activator surfactants, leaf wetters, defoamers, and water softeners, e.g., ammonium sulfate. This listing is merely exemplary and other optional components are also contemplated.

The active ingredient may vary widely, and many active ingredients are known in the art. Active ingredients are compounds that are known to have an effect on the substrate to which the active ingredient is applied. Generally speaking, an active ingredient, e.g., an agriculturally active ingredient, is a substance (present in a pesticide composition) that is biologically active. As one explanation, according to EPA, the term "active ingredient" has been defined in FIFRA as a compound that prevents, destroys, repels or mitigates a pest. More than one active ingredient may be present. In one embodiment, the active ingredient is selected form the group consisting of herbicides, pesticides, fungicides, insecticides, acaricides, nematocides, foliar nutrients, defoliants, plant growth regulators, molluscidcides. In one embodiment, the active ingredient is selected from the group consisting of 2,4-D Dichlorophenoxyacetic acid (2,4-D), glyphosate, dicamba, triclopyr, imazapyr, sulfometuron, methyl, fluridone, clopyralid, picloram, hexazinone, chlorpyriphos, carbaryl, methomyl, ethepon, fosamine, benomyl, ferbam, zineb. In a preferred embodiment, the active ingredient is selected from the group consisting of glyphosate, 2,4-D, dicamba and mixtures thereof.

The liquid carrier may vary widely. Many liquid carriers are known in the art. Suitable liquid carriers include water, synthetic and vegetable oils. Preferably, the liquid carrier comprises water.

In some embodiments, the active ingredient is present in an amount from 0.5 wt % to 5 wt %, e.g., from 0.5 wt % to 4 wt %, from 1 wt % to 4 wt %, or from 1 wt % to 3 wt %. In terms of upper limits, the active ingredient may be present in an amount less than 5 wt %, e.g., less than 4 wt %, less than 3, wt %, or less than 2 wt %. In terms of lower limits, the active ingredient may be present in an amount greater than 0.5 wt %, e.g., greater than 1 wt %, greater than 2 wt %, or greater than 3 wt %. As noted above, the agricultural spray composition may comprise multiple active ingredients. The ranges and limits listed above apply to individual active ingredients or to combinations of the individual active ingredients.

The adjuvant may be present in an amount from 0.01 wt % to 15 wt %, e.g., from 0.01 wt % to 10 wt %, from 0.01 wt % to 5 wt %, from 0.01 wt % to 1.5 wt %, from 0.02 wt % to 2 wt %, or from 0.05 wt % to 1.5 wt %. In terms of limits, the adjuvant may be present in an amount less than 15 wt %, e.g., less than 10 wt %, less than 5 wt %, less than 1.5 wt %, less than 1, wt %, or less than 0.5 wt %. The adjuvant may be present in an amount greater than 0.01 wt %, e.g., greater than 0.02 wt %, greater than 0.05, wt %, or greater than 1 wt %. Weight percentage ranges and limits are based on the total weight of the agricultural spray composition.

In some cases, the agricultural spray composition may be in the form of a concentrate, e.g., a low water version, which may be diluted by the user. In such cases, the active ingredient may be present in an amount from 20 wt % to 99 wt %, e.g., from 30 wt % to 95 wt %, from 50 wt % to 95 wt %, or from 40 wt % to 85 wt %. In terms of upper limits, the active ingredient may be present in an amount less than 99 wt %, e.g., less than 95 wt %, less than 90, wt %, or less than 85 wt %. In terms of lower limits, the active ingredient may be present in an amount greater than 20 wt %, e.g., greater than 30 wt %, greater than 40 wt %, or greater than 50 wt %.

The adjuvant may be present in an amount from 0.1 wt % to 40 wt %, e.g., from 1 wt % to 30 wt %, from 1 wt % to 20 wt %, or from 5 wt % to 15 wt %. In terms of upper limits, the adjuvant may be present in an amount less than 40 wt %, e.g., less than 30 wt %, less than 20, wt %, or less than 15 wt %. In terms of lower limits, the adjuvant may be present in an amount greater than 0.1 wt %, e.g., greater than 1 wt %, or greater than 5 wt %.

Other components, e.g., water softeners, may also be present. In such cases, the other ingredients may be present in an amount from 1 wt % to 50 wt %, e.g., from 3 wt % to 40 wt %, from 5 wt % to 35 wt %, or from 10 wt % to 20 wt %. In terms of upper limits, the other ingredients may be present in an amount less than 50 wt %, e.g., less than 40 wt %, less than 35, wt %, or less than 20 wt %. In terms of lower limits, the active ingredient may be present in an amount greater than 1 wt %, e.g., greater than 3 wt %, greater than 5 wt %, or greater than 10 wt %/o.

The present invention also relates to a process for treating an agricultural product. The process comprises the step of spraying the inventive agricultural spray composition on the agricultural product. Preferably, the spraying forms a plurality of droplets and the droplets have an average droplet size from 50 µm to 1000 µm, e.g., from 100 µm to 750 µm, from 100 µm to 600 µm, from 100 µm to 400 µm, 150 µm to 350 µm, or from 200 μm to 300 μm. In one embodiment, from 1 vol % to 10 vol %, e.g., from 2 vol % to 8 vol % or from 4 vol % to 6 vol %, of the droplets have a droplet size less than 105 μm. In one embodiment, no more than 10 vol %, e.g., no more than 8 vol % or no more than 6 vol %, of the droplets have a droplet size less than 105 μm. In one embodiment, more than 1 vol %, e.g., more than 2 vol % or more than 4 vol %, of the droplets have a droplet size less than 105 μm.

In one embodiment, the agricultural spray composition, when sprayed, yields a low number of driftable fines, e.g., droplets that are less than 150μ, e.g., less than 105μ in size (droplet diameter). Preferably, the weight percent of droplets less than 105μ in size is less than 10 wt %, e.g., less than 9 wt %, less than 8 wt %, less than 7 wt %, less than 6 wt %, less than 5 wt %, less than 4 wt %, less than 3 wt %, less than 2 wt %, or less than 1 wt %. In some embodiments, the agricultural spray composition, when sprayed, provides a high Dv10, which is the size (μm) at which 10% of the spray volume is of the reported size or smaller. Dv50 and Dv90 are similar statistics, but with different percentages, i.e., 50% and 90%, respectively). In some embodiments, the agricultural spray composition provides for a Dv50 greater than 125μ, e.g., greater than 150μ, greater than 175μ, greater than 200μ, greater than 250μ, greater than 260μ, greater than 270μ, greater than 275μ, or greater than 280μ. In some embodiments, the agricultural spray composition, when sprayed, provides a low relative span. Relative span is a measure of the width of the droplet size distribution, e.g., the ratio of difference between Dv90 and Dv10 to the Dv50. For example the agricultural spray composition may provide a relative span less than 1.5, e.g., less than 1.4, less than 1.3, less than 1.2, less than 1.1, less than 1.0, less than 0.95, less than 0.90, or less than 0.85.

The combination of polymer dispersion and plasticizer in the adjuvant provides for agricultural spray compositions that have beneficial combinations of features. For example, the agricultural spray compositions may droplets having a low weight percentage of driftable fines, a low relative span, and a high Dv10. For example, the agricultural spray composition, when sprayed, may yield droplets having less than 10 wt % droplets less than 105μ in size, a relative span less than 1.5, and a Dv50 greater than 125μ. As another example, the agricultural spray composition, when sprayed, may yield droplets having less than 7 wt % droplets less than 105μ in size, a relative span less than 1.2, and a Dv50 greater than 250μ. Other combinations of limits/ranges (as may be discussed individually herein) are contemplated. The individual limits/ranges discussed herein may be combined to describe other beneficial combination features, e.g., a combination of a relative span less than 1.2 and an evaporation rate ranging from 1.0% weight loss/min to 8% weight loss/min.

In some cases, conventional emulsifiable oil adjuvants, when utilized in an agricultural spray composition, may be able to achieve the preferred combination of a low weight percentage of driftable fines, a low relative span, and/or a high Dv10. Such products, however, form micro-emulsion droplets may become unstable and phase separate over a time. These droplets may also become too large to spray via agricultural spray nozzles. And the droplets diameter remains substantially constant over time. Also, in contrast to the inventive adjuvants, for emulsifiable oils, higher amounts of surfactants are needed to emulsify the oils. The higher loading of surfactants could potentially increase phytotoxicity and generate foam during mixing which may require the use of defoamers etc. that could add cost and complexity to the process. In contrast, the polymer dispersions according to this invention demonstrate superior performance, and also have much smaller particle diameters and do not require higher amounts of surfactants (due to the combination of polymer dispersion, plasticizer, and active ingredient).

In one embodiment, the agricultural composition has a slow evaporation rate. The evaporation rate may be measured using a Thermal gravimetric analysis (TGA) instrument, and the evaporation rate (of the droplets) may range from 1.0% weight loss/min to 8% weight loss/min, e.g., from 1.2% weight loss/min to 5% weight loss/min or from 1.2% weight loss/min to 2.5% weight loss/min. The drying time may range from 25 min to 100 min, e.g., from 35 min to 90 min, or from 40 min to 87 min. The dry time and evaporation rate may be measured using a TGA (Discovery TGA, TA Instruments). 40 μL of agriculture spray composition may be used. The temperature is ramped at 20° C./minute to 40° C., and the isotherm is collected for 75 minutes or until completely evaporated. Air is purged at a purge rate of 25 mL/min. The data are analyzed by using a linear fit to the evaporation data at 40° C. and using the slope to the linear fit as the average evaporation rate.

The surface tension of the droplets may decrease by less than 10 mN/m-min, e.g., less than 5 mN/m-min or less than 2 mN/m-min. As one example, an Attension Theta optical tensiometer with a manual syringe may be used to measure surface tension and contact angle. Data may be recorded with 40 frames/sec speed for 60 sec. Droplet sizes may be kept around 6 μm. If a pendant drop of 6 μm is not formed, the volumes of droplets may be increased accordingly.

The droplets may have an average contact angle from 35° to 75°, e.g., from 40° to 70°, or from 45° to 65°. As one example, contact angle may be determined using an Advanced Goniometer with PP texturized film as substrate.

The spread diameter may range from 4.5 mm to 7.0 mm, e.g., from 5 mm to 6.5 mm or from 5.5 mm to 6.0 mm. Optical Microscope with Coaxial Reflected Light. PP texturized film as substrate. 20 μL of sample was used The particle size distribution (PSI)) measurements of the adjuvant may be conducted using a Mastersizer Microplus laser diffraction instrument from Malvern. The scatter data may be evaluated using the "Polydisperse Mie" model provided by Malvern. Particle sizes are given in μm. Particle fraction proportions were calculated from peak areas of the PSD curves.

The present invention also relates to a method for producing an agricultural spray composition. The method comprises the steps of providing the vinyl ester-based polymer dispersion and adding to the vinyl ester-based polymer dispersion a plasticizer to form the adjuvant. The method further comprises the step of adding to the adjuvant an active ingredient to form the agricultural spray composition. The adding step may comprise adding to the vinyl ester-based polymer dispersion at least 15 wt % plasticizer, based on the total weight of the spray adjuvant. A liquid carrier may also be added to the adjuvant.

EXAMPLES

The following examples are non-limiting.

Wind tunnel testing was conducted in the United States Department of Agriculture, Agriculture Research Service, Aerial Application Technology (AAT) group's low speed wind tunnel. The low speed wind tunnel (1.2 m×1.2 m×12.2 m) had an operational capacity of 0-8 m/s with airflow generated from a 1 m diameter with an axial flow fan. The nozzle body was positioned on the vertical traverse but offset 15 cm to prevent interference with airflow. Sprayed material was carried through the last 2.4 m section of tunnel and exited the hanger that housed the tunnel. Spray nozzles are fed from 19L stainless steel pressure tanks that were pressurized using air compressor. The pressure was controlled via a pressure regulator and measured using an electronic pressure gauge (PX409-100GUSB), Omega Engineering, Stamford, Conn.) that was positioned within 20 cm of the nozzle outlet. A standard flat fan nozzle XR11003 was used at 40 psi nozzle pressure and 15 mph wind speed.

The spray droplets were analyzed with a Sympatec Helos Vario KR particle size analyzer (Sympatec, Inc., Clausthal, Germany). The system uses laser diffraction to analyze particle size. The Helos system uses a 623 nm He:Ne laser and was fitted with a lens (denoted by manufacturer as R7) with a dynamic range of 0.5-3500 microns divided across 32 sizing bins.

The width of the nozzle plume was analyzed by moving the nozzle across the laser by means of a linear actuator. Each of the treated spray was replicated three times. Each replication consisted of a single traverse of either the nozzle or laser such that the whole spray plume was sampled. For the low speed (15 MPH) testing, the laser was positioned horizontally and centered across the tunnel outlet downwind of the spray nozzle with the spray nozzle being traversed during each measurement. The data shown in the following tables are average values.

The following measurements are shown in the results. Dv10 is the micron size (μm) at which 10% of the spray volume is of the reported size or smaller. Dv50 and Dv90 are similar statistics, but with different percentages. The percent less than 105 μm (Pct<105 μm) is the percentage of spray volume that is 105 μm and smaller, with percent less than 150 μm (Pct<150 μm), 210 μm (Pct<210 μm) being similar measurements, but with different particle sizes. The relative span, which is a measure of the width of the droplet size distribution, is the ratio of difference between Dv90 and Dv10 to the Dv50, i.e., Relative Span=(Dv90−Dv10)/Dv50. The mean separations were conducted at the p=0.05 level using a Tukey adjustment. More detailed description of the wind tunnel and the measurement conditions are provided in, "Measuring Droplet Size of Agricultural Spray Nozzles-Measurement Distance and Airspeed Effects," Bradley K. Fritz, W, C. Hoffman, W. E. Bagley, G. R. Kruger, Zbigniew Czaczyk and R. S. Henry, Atomization and Sprays, 24 (9): 747-760 (2014).

Example 1: Adjuvant (Concentrate)

The following procedure was used to prepare the adjuvant concentrates used in the all examples. The polymer dispersion was placed in a plastic container and vigorously agitated at 500 rpm. The plasticizer was slowly added to the polymer dispersion over a period of 10 minutes into the vortex of the mixing blade. Agitation was slowly increased during the course of plasticizer addition from 500 rpm to about 1000 rpm. Once all the plasticizer preferentially goes into the polymer phase as evidenced by the homogeneous appearance of the mixture, 10 grams of water was added to the mixture to thin it down and make it pourable from the container. The percent solids of the adjuvant concentrate was measured by heating 1 gram of the adjuvant concentrate at 110° C. for 1 hr. The weight percent solids of the adjuvant concentrates were around 62% to 72%. The pH of the adjuvant concentrates shown in the following examples were between 4 to 5.5

TABLE 1

| Component | Adjuvant 1 Amount, g | Adjuvant 2 Amount, g |
|---|---|---|
| Dur-O-Set C-325[1] (Polymer Dispersion; Colloid Stabilized) | 60 | |
| Celvoset PL-1000[1] (Plasticizer) | 40 | 30 |
| Avicor 3251 (Polymer Dispersion; Surfactant Stabilized) | | 60 |
| Water | 10 | 10 |

[1]Celanese Corporation

Example 1: Agricultural Spray Composition

An agricultural spray composition ("ASC") was prepared in accordance with Table 2 using the adjuvant made from the components shown in Table 1, 0.5% by weight of the adjuvant concentrate solids were used. Dur-O-Set C-325 is a colloid stabilized polyvinyl acetate homopolymer (PVAc) and Avicor 325 is non-ionic surfactant stabilized polyvinyl acrylic copolymer (PVA).

TABLE 2

| Touchdown Hi-Tech[1] (Glyphosate) (active ingredient) | 3.4% |
|---|---|
| Base Camp Amine 4[1] (2,4 D) (active ingredient) | 1.5% |
| Adjuvant 1 or 2 (concentrate) | 0.5% |
| Ammonium Sulfate[1] (water softener) | 1.02% |
| Water | Make up to 100% |

[1]Wilbur Ellis Company

The agricultural spray composition was tested as described above. Comparative Examples using only colloid stabilized polymer dispersion (Comparative A1), only surfactant stabilized polymer dispersion (Comparative A2), and only plasticizer (Comparative B) were also tested. The results are presented in Table 3. As shown in Table 3, Comparative A generates more <105 mm fines than Comparative B. However when they are blended to form a plasticized polymer mixture, the amount of fines, <105 mm, generated drop significantly. Similarly, the Dv50 size increases and relative span decreases for the Examples using Adjuvants 1 and 2 to Comparative Examples using Comparatives A and B.

Generally speaking, it appears that plasticizing the polymer dispersion with plasticizer advantageously increases the median particle size, e.g., reduces driftable fines, while narrowing the droplet size distribution and relative span and increasing Dv50 size. This unique combination of features leads to a highly desirable agricultural spray composition. This effect was observed with both colloid stabilized PVAc and surfactant stabilized PVA.

TABLE 3

| Adjuvant used in ASC | Adjuvant Loading | Dv10, μm | Dv50, μm | Dv90, μm | Pct, <105 μm | Pct, <150 μm | Pct, <210 μm | Pct, <730 μm | Relative Span |
|---|---|---|---|---|---|---|---|---|---|
| Comparative A1 | 0.5% | 101 | 229 | 397 | 11.01 | 23.74 | 43.68 | 100 | 1.29 |
| Comparative A2 | 0.5% | 103.5 | 232.0 | 395.7 | 10.38 | 22.9 | 42.7 | 100 | 1.26 |
| Comparative B | 0.5% | 124 | 248 | 400 | 6.17 | 16.48 | 36.47 | 100 | 1.11 |
| Adjuvant 1 | 0.5% | 137 | 261 | 399 | 4.66 | 12.5 | 30.68 | 100 | 1 |
| Adjuvant 2 | 0.5% | 129 | 257 | 410 | 5.4 | 14.75 | 33.56 | 100 | 1.09 |

Comparative Example Adjuvants and Spray Compositions C—H

Comparative agricultural spray compositions were prepared using sample adjuvants C—H, as shown in Table 4. The comparative agricultural spray compositions were prepared in a manner similar to the preparation discussed above.

TABLE 4

| Comparative Example | Adjuvant | Chemistry | Loading, wt % |
|---|---|---|---|
| Comparative C | Bond[1] | SBR-Based Emulsion | 0.1 |
| Comparative D | LI700[2] | Lecithin, methyllactic acid and alkyl phenol ethoxylate | 0.39 |
| Comparative E | xanthum gum[3] | Water swellable polysaccharide | 0.1 |
| Comparative F | EDT Concentrate[3] | Water swellable polyacrylamide polymer | 1.06 |
| Comparative G | In Place[3] | Water-in-oil Invert Emulsion | 0.275 |
| Comparative H | Interlock[4] | Emulsifyable vegetable oil concentrate | 0.275 |

[1]Nufarm Australia Limited
[2]Loveland Products
[3]Wilbur Ellis Company
[4]Winfield Solutions LLC Table 5 shows the wind tunnel droplet size distribution for the comparative agricultural spray compositions using available conventional adjuvants C—H (used at the mid-point of their label rate). Results for the Examples using Adjuvants 1 and 2 are also shown.

TABLE 5

| Adjuvant used in ASC | Dv10, μm | Dv50, μm | Dv90, μm | Pct, <105 μm | Pct, <150 μm | Pct, <210 μm | Pct, <730 μm | Relative Span |
|---|---|---|---|---|---|---|---|---|
| Comparative C | 99 | 226 | 391 | 11.46 | 24.53 | 44.78 | 99.83 | 1.29 |
| Comparative D | 132 | 251 | 386 | 5.09 | 13.8 | 33.53 | 100 | 1.01 |
| Comparative E | 124 | 297 | 526 | 6.67 | 15.13 | 29.07 | 99.8 | 1.35 |
| Comparative F | 106 | 233 | 400 | 9.65 | 22.34 | 42.27 | 100 | 1.26 |
| Comparative G | 128 | 253 | 404 | 5.51 | 15.21 | 34.72 | 100 | 1.1 |
| Comparative H | 133 | 258 | 407 | 4.86 | 13.82 | 32.77 | 99.83 | 1.06 |
| Adjuvant 1 | 137 | 261 | 399 | 4.66 | 12.5 | 30.68 | 100 | 1 |
| Adjuvant 2 | 129 | 257 | 410 | 5.4 | 14.75 | 33.56 | 100 | 1.09 |

In general, polymer based adjuvants (Comparatives C, F, and F) give much higher <105 μm droplet than emulsifiable oil based adjuvants (Samples D, G, and H). Within the polymer based adjuvants, latex based Sample C gives significantly higher <105 μm fines than soluble polymers such as xanthum gum or EDT. Similarly, the median droplet size (Dv50) of Sample C is smaller than both the soluble polymer based and emulsifiable oil based adjuvants. The relative span of the polymeric adjuvants was in general much higher than oil based adjuvants. Comparing the soluble polymer and oil based adjuvant it is clear that even with similar median droplet size (Dv50), the polymeric dispersants give much broader droplet distribution, higher relative span. The much larger droplets generated because of the broader distribution are likely to reduce the overall efficacy of the spray composition because larger droplets have a greater tendency to bounce-off of leaves.

Although Comparatives D, G, and H may provide some suitable performance characteristics, these compositions do not comprise the polymer dispersion/plasticizer combination of the present invention. Comparatives D, G, and H are emulsifiable oils and suffer from several disadvantages. For example, when mixed with water and active ingredient to form agricultural spray composition, these types of adjuvants form micro-emulsion droplets that become unstable and phase separate over a time or that become too large to spray via agricultural spray nozzles. In contrast, the polymer dispersions according to this invention demonstrate the beneficial performance, and also have much smaller particle diameters, which remains substantially constant over time. Also, in contrast to the inventive adjuvants, for emulsifiable oils, larger amounts of surfactants are needed to emulsify the oils. The higher loading of surfactants could potentially increase phytotoxicity and generate foam during mixing which may require the use of defoamers etc. that could add cost and complexity to the process.

Example 2

An agricultural spray composition was prepared using the components shown in Table 2, with the exception that the amount of adjuvant loading in the formulation was varied as shown in Table 6. The samples were tested and the results are shown in Table 6. The results show that the inventive adjuvants are very effective in increasing the median droplet size and reducing the driftable fines (Pct. <105 μm) even at very low levels of use at or below 0.1% by weight of the adjuvant concentrate solids. The 0.1% use level corresponds to 50% of the mid-point of the label use rate of the commercially available oil based adjuvants showing that the adjuvant composition of this invention is at least twice as effective as the oil based commercially available adjuvants while giving equivalent or narrower droplet distribution (relative span being similar or smaller than the oil based adjuvants). Further, even at usage level corresponding to 0.01% by weight of the adjuvant concentrate solids, the inventive adjuvants appear to generate lower <105 μm droplets than the commercially available polymeric adjuvants.

TABLE 6

| Adjuvant used in ASC | Adjuvant Loading | Dv10, μm | Dv50, μm | Dv90, μm | Pct, <105 μm | Pct, <150 μm | Pct, <210 μm | Pct, <730 μm | Relative Span |
|---|---|---|---|---|---|---|---|---|---|
| Adjuvant 1 | 0.01% | 125 | 250 | 405 | 5.99 | 16.29 | 35.93 | 100 | 1.12 |
| Adjuvant 1 | 0.1% | 136 | 262 | 405 | 4.64 | 12.84 | 30.95 | 100 | 1.02 |
| Adjuvant 1 | 0.5% | 137 | 261 | 399 | 4.66 | 12.5 | 30.68 | 100 | 1 |
| Adjuvant 1 | 1.0% | 136 | 255 | 387 | 4.58 | 12.84 | 32.07 | 100 | 0.99 |

Example 3

Additional adjuvants were prepared in accordance with Table 7. Additional rheology modifiers were added to the adjuvant concentrate, and the ability to reduce the driftable fines was unaffected. Attagel 50 solution was prepared mixing 10% by weight of Attagel 50 powder and 90% by weight water under vigorous stirring. The stirring was stopped after 10 minutes. PVOH solution was prepared by dissolving 5 grams of Celvol 165SF in cold water in a jacketed stainless steel reactor. Complete dissolution of Celvol 165SF, as evidenced by the formation of a clear liquid, was achieved by heating the solution to a temperature of 185° F. (85° C.), and holding it for 30 minutes under vigorous agitation. The solids weight percentage of the PVOH solution was 5.77%.

TABLE 7

| Component | Adjuvant 3 Amount, g | Adjuvant 4 Amount, g |
|---|---|---|
| Dur-O-Set C-325 | 42 | 41.5 |
| Celvoset PL-10001 | 27.9 | 27.63 |
| Attagel 50 solution[1] | 30.3 | 60 |
| PVOH solution[2] |  | 26 |
| Water |  | 5 |

[1]BASF Corporation
[2]Sekisui Specialty Chemicals America

The samples were tested and the results are shown in Table 8.

TABLE 8

| Adjuvant used in ASC | Dv10, μm | Dv50, μm | Dv90, μm | Pct, <105 μm | Pct, <150 μm | Pct, <210 μm | Pct, <730 μm | Relative Span |
|---|---|---|---|---|---|---|---|---|
| Adjuvant 3 | 134 | 262 | 409 | 4.77 | 13.23 | 31.31 | 100 | 1.05 |
| Adjuvant 4 | 132 | 260 | 411 | 5.01 | 13.96 | 32.43 | 100 | 1.07 |

Example 4

Additional adjuvants were prepared using Dur-O-Set C-325 and a variety of commercially available synthetic, and vegetable oil based plasticizers, as shown in Table 9. Agricultural spray compositions were prepared using these adjuvants, as described above.

TABLE 9

| Component | Adjuvant 5 Amount, g | Adjuvant 6 Amount, g | Adjuvant 7 Amount, g | Adjuvant 8 Amount, g | Adjuvant 9 Amount, g | Adjuvant 10 Amount, g |
|---|---|---|---|---|---|---|
| Dur-O-Set C-325 | 60 | 60 | 90 | 80 | 60 | 60 |
| Optifilm Enhancer 400[1] | 30 |  |  |  |  |  |
| Loxanol EFC 200[2] |  | 30 |  |  |  |  |
| Soygold 2500[3] |  |  | 10 |  |  |  |
| Soyanol SGE 40[4] |  |  |  | 20 |  |  |
| Dioctyl phthalate[1] |  |  |  |  | 30 |  |
| ADM CA 118 |  |  |  |  |  | 40 |
| Water |  | 10 | 10 |  | 10 | 10 |

[1]Eastman Corporation
[2]BASF Corporation
[3]Ag Processing Inc.
[4]Soy Technologies LLC
[5] Archer Daniels Midland Company These agricultural spray compositions were tested and the results are shown in Table 10. As shown, these agricultural spray compositions substantially reduce the driftable fines as compared to the commercially available adjuvants. It appears that the reduction in <105 mm droplets is achieved by increasing the median droplet size without significantly broadening the droplet size distribution.

TABLE 10

| Adjuvant used in ASC | Dv10, μm | Dv50, μm | Dv90, μm | Pct, <105 μm | Pct, <150 μm | Pct, <210 μm | Pct, <730 μm | Relative Span |
|---|---|---|---|---|---|---|---|---|
| Adjuvant 5 | 137 | 257 | 395 | 4.45 | 12.69 | 31.67 | 100 | 1 |
| Adjuvant 6 | 125 | 235 | 376 | 5.79 | 17.12 | 39.94 | 100 | 1.07 |
| Adjuvant 7 | 127 | 251 | 401 | 5.77 | 15.59 | 35.27 | 100 | 1.09 |
| Adjuvant 8 | 131 | 255 | 402 | 5.18 | 14.31 | 33.48 | 100 | 1.06 |
| Adjuvant 9 | 134 | 256 | 401 | 4.69 | 13.41 | 32.71 | 100 | 1.04 |
| Adjuvant 10 | 148 | 274 | 415 | 3.26 | 10.35 | 27 | 100 | 0.97 |
| Comparative C | 99 | 226 | 391 | 11.46 | 24.53 | 44.78 | 99.83 | 1.29 |
| Comparative D | 132 | 251 | 386 | 5.09 | 13.8 | 33.53 | 100 | 1.01 |
| Comparative E | 124 | 297 | 526 | 6.67 | 15.13 | 29.07 | 99.8 | 1.35 |
| Comparative F | 106 | 233 | 400 | 9.65 | 22.34 | 42.27 | 100 | 1.26 |
| Comparative G | 128 | 253 | 404 | 5.51 | 15.21 | 34.72 | 100 | 1.1 |
| Comparative H | 133 | 258 | 407 | 4.86 | 13.82 | 32.77 | 99.83 | 1.06 |

While the invention has been described in detail, modifications within the spirit and scope of the invention will be readily apparent to those of skill in the art. It should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with other embodiments as will be appreciated by one of ordinary skill in the art. Furthermore, those of ordinary skill in the art will appreciate that the foregoing description is by way of example only, and is not intended to limit the invention.

We claim:

1. An agricultural spray composition, comprising:
   an adjuvant comprising:
      an aqueous vinyl ester-based polymer dispersion, and
      a plasticizer; and
   an active ingredient dissolved in an aqueous phase.

2. The agricultural spray composition of claim 1, wherein vinyl ester-based polymer dispersion is stabilized by at least one of a protective colloid and a surfactant.

3. The agricultural spray composition of claim 1, wherein the vinyl ester-based polymer dispersion and the plasticizer form an adjuvant and the adjuvant is present in amount from 0.01 to 15 wt %, based on the total weight of the spray composition.

4. The agricultural spray composition of claim 3, wherein the adjuvant comprises greater than 15 wt % plasticizer, based on total weight of the adjuvant.

5. The agricultural spray composition of claim 3, wherein the adjuvant comprises less than 85 wt % vinyl ester-based polymer dispersion, based on total weight of the adjuvant.

6. The agricultural spray composition of claim 1, wherein the vinyl ester-based polymer dispersion comprises an aqueous dispersion of a polymer produced from one or more monomers, at least one of the monomers comprising a vinyl ester of a carboxylic acid.

7. The agricultural spray composition of claim 6, wherein the at least one of the monomers comprises a vinyl ester of a carboxylic acid and having up to 20 carbon atoms.

8. The agricultural spray composition of claim 1, wherein the plasticizer is selected from the group consisting of an epoxidized methyl ester of soy oil, methyl ester of soy oil, triethylene glycol diester, polyalkylene glycols, polyether polyols, esters of canola oil, esters of castor oil, ester oils, 2,2,4-trimethyl-1,3-pentanediol monoisobutyrate, phthalates, adipic acid polyesters, trimellitates, adipates, epoxy esters, polyetheresters, epoxidized soy esters, benzoates, dipropylene glycol dibenzoate, diethylene glycol dibenzoate, and mixtures thereof.

9. The agricultural spray composition of claim 1, wherein the active ingredient is selected from the group consisting of herbicides, pesticides, fungicides, insecticides, acaricides, nematocides, foliar nutrients, defoliants, plant growth regulators, molluscidcides.

10. The agricultural spray composition of claim 1, wherein the active ingredient is selected from the group consisting of 2,4-D Dichlorophenoxyacetic acid (2,4-D), glyphosate, dicamba, triclopyr, imazapyr, sulfometuron, methyl, fluridone, clopyralid, picloram, hexazinone, chlorpyriphos, carbaryl, methomyl, ethepon, fosamine, benomyl, ferbam, zineb, and mixtures thereof.

11. The agricultural spray composition of claim 1, wherein the active ingredient is present in an amount from 0.5 to 5 wt %, based on total weight of the spray composition.

12. The agricultural spray composition of claim 1, further comprising a liquid carrier.

13. The agricultural spray composition of any one of claim 12, wherein the liquid carrier is water.

14. The agricultural spray composition of claim 1, wherein the plasticizer is present in an amount ranging from 15 wt % to 70 wt %, based on the weight of the adjuvant.

15. An agricultural spray composition, comprising:
   an adjuvant comprising:
      an aqueous vinyl ester-based polymer dispersion comprising vinyl-ester based polymer colloid particles comprising plasticizer and being dispersed in water; and
   an active ingredient.

16. The agricultural spray composition of claim 15, wherein the plasticizer is present in an amount ranging from 15 wt % to 70 wt %, based on the weight of the adjuvant.

* * * * *